(12) United States Patent
Yuan et al.

(10) Patent No.: US 10,259,909 B2
(45) Date of Patent: Apr. 16, 2019

(54) METHOD FOR PREPARING GLATIRAMER ACETATE

(71) Applicant: HYBIO PHARMACEUTICAL CO., LTD., Shenzhen (CN)

(72) Inventors: Huixing Yuan, Shenzhen (CN); Guotao Li, Shenzhen (CN); Jian Liu, Shenzhen (CN); Yaping Ma, Shenzhen (CN); Jiancheng Yuan, Shenzhen (CN)

(73) Assignee: HYBIO PHARMACEUTICAL CO., LTD., Shenzhen (CN)

(*) Notice: Subject to any disclaimer, the term of this patent is extended or adjusted under 35 U.S.C. 154(b) by 243 days.

(21) Appl. No.: 15/513,995

(22) PCT Filed: Nov. 26, 2015

(86) PCT No.: PCT/CN2015/095606
§ 371 (c)(1),
(2) Date: Mar. 24, 2017

(87) PCT Pub. No.: WO2016/045646
PCT Pub. Date: Mar. 31, 2016

(65) Prior Publication Data
US 2017/0298180 A1    Oct. 19, 2017

(30) Foreign Application Priority Data
Sep. 26, 2014 (CN) .......................... 2014 1 0504852

(51) Int. Cl.
*C08G 69/04* (2006.01)
*C08G 69/36* (2006.01)
*C07K 2/00* (2006.01)

(52) U.S. Cl.
CPC ............... *C08G 69/04* (2013.01); *C07K 2/00* (2013.01); *C08G 69/36* (2013.01)

(58) Field of Classification Search
None
See application file for complete search history.

(56) References Cited

U.S. PATENT DOCUMENTS

| 5,800,808 A | 9/1998 | Konfino et al. |
| 2007/0141663 A1* | 6/2007 | Ding .................. C07K 1/02 435/68.1 |
| 2008/0118553 A1* | 5/2008 | Frenkel ............... C07K 14/001 424/451 |
| 2010/0036092 A1* | 2/2010 | Hsiao ................... C07K 1/02 530/335 |

FOREIGN PATENT DOCUMENTS

| CN | 1310673 C | 4/2007 |
| CN | 102718963 A | 10/2012 |
| CN | 103169670 A | 6/2013 |
| CN | 103641897 A | 3/2014 |
| CN | 101166754 B | 4/2014 |
| CN | 104844697 A | 8/2015 |
| WO | WO2010115175 A1 | 10/2010 |
| WO | WO2011022063 A1 | 2/2011 |

OTHER PUBLICATIONS

CN103641897 English Machine translation created Dec. 29, 2018 (Year: 2018).*
CN104844697 English Machine Translation created Dec. 29, 2018 (Year: 2018).*
CN104844697 Derwent Abstract, Accession No. 2015-61329F, accessed Dec. 29, 2018 (Year: 2018).*
Li Rui, et al. Advances in the treatment of multiple sclerosis, Practical Hospital Clinic Magazine. May 31, 2013. pp. 1-5. vol. 10.

* cited by examiner

*Primary Examiner* — Christopher M Rodd
(74) *Attorney, Agent, or Firm* — Gokalp Bayramoglu

(57) ABSTRACT

The present invention discloses a method for preparing glatiramer acetate, comprising: (1) dissolving L-alanine NCA, L-tyrosine NCA, L-glutamic acid-γ-benzyl ester NCA, and L-ε-trifluoroacetyl-lysine NCA in 1,4-dioxane as solvent, stirring until a clarified solution is formed; (2) adding diethylamine for catalysis, stirring at 20-25° C., then slowly pouring the reaction solution into water, collecting the produced white product; (3) adding the obtained product to a solution of hydrobromic acid in acetic acid, stirring at 23.0-25.0° C., pouring the reaction solution into purified water for quenching and stirring, subjecting the mixture to suction filtration to obtain a yellow solid, after repeating 3-5 times, subjecting the solid to blast drying to remove the moisture therein; and (4) dissolving the solid obtained in step (3) in a 1M piperidine aqueous solution at room temperature and stirring, subjecting the obtained solution to dialysis, adding glacial acetic acid to adjust the pH to 5.5-7.0, and lyophilizing.

19 Claims, 3 Drawing Sheets

METHOD FOR PREPARING GLATIRAMER ACETATE

CROSS REFERENCE TO RELATED APPLICATIONS

This application is the national phase of International Application No. PCT/CN2015/095606, filed on Nov. 26, 2015, which is based upon and claims priority to Chinese Patent Application No. 201410504852.4, filed on Sep. 26, 2014, the entire contents of which are incorporated herein by reference.

TECHNICAL FIELD

The present invention relates to the field of medicine, more particular, to a method for preparing glatiramer acetate.

BACKGROUND

Autoimmune diseases refer to phenomena that the immune system of an organism treats some of the organism's own tissues as "foreign objects" and attacks them. Normally, such diseases can be alleviated by hindering the response of T cells and B cells of the organism to its own tissues. These early immune reactions are prompted by the binding of antigens to MHC molecules and are performed by T cells. The autoimmune diseases mean that the organism's own tissues and proteins are treated as "self-antigens" and are attacked by the organism's immune system. Taking multiple sclerosis—a disease caused by attack of the immune system on the myelin sheath that isolates and protects nerves—for example, when it progresses to an extent that the myelin sheath is lost, neurons and motor nerves will lose their function. Other diseases, such as systemic lupus erythematosus, rheumatoid arthritis, autoimmune hemolytic anemia, also belong to this kind of diseases.

Many drugs have been developed for the treatment of autoimmune diseases, including multiple sclerosis. Glatiramer acetate (also known as copolymer-1, GA) is a mixture of polymers having different molecular weights produced by peptide bond polymerization of alanine, glutamic acid, lysine and tyrosine. The molar ratio of the four amino acids in this mixture is about 0.392 to 0.462:0.129 to 0.153:0.300 to 0.374:0.086 to 0.100 (Ala:Glu:Lys:Tyr), and the average molecular weight of the copolymer in the mixture is about 5,000 to 9,000 daltons. Glatiramer acetate is used for treating patients suffering from intermittent recurrent multiple sclerosis, and for reducing the frequency of recurrence.

Several existing patents (U.S. Pat. No. 5,800,808, CN1310673C, etc.) describe in detail the preparation method, including reacting the protected polymer with 33% of hydrobromic acid in acetic acid. This deprotecting reaction removes the γ benzyl protective group from the 5-carboxylate ester of the glutamic acid residue and cleaves the polymer into smaller polymers to form a trifluoroacetyl polypeptide. The time required for obtaining a proper average molecular weight of GA between 5,000 and 9,000 daltons depends on the reaction temperature and the molecular weight pattern of the protected glatiramer acetate. The deprotection occurs at a temperature between 20° C. and 28° C.

CN101166754B further describes a method, wherein the protected polymer is synthesized, and then it is deprotected with a solution of hydrobromic acid in acetic acid which contains less than 0.5% of free bromine and less than 1000 ppm of metal ions impurities, such that glatiramer acetate is prepared.

However, in a process of practically optimizing the synthesis method of the polymer, the inventors found that this method is not very sensitive to the impurity content and concentration of the solution of hydrobromic acid in acetic acid. Additionally, the thus obtained product is not very satisfactory, and the purity of the obtained glatiramer acetate sample is below the high purity standard required for pharmaceutical use.

SUMMARY OF INVENTION

The present invention relates to a method for preparing highly purified glatiramer acetate, comprising the following steps:
(1) dissolving L-alanine NCA, L-tyrosine NCA, L-glutamic acid-γ-benzyl ester NCA, and L-ε-trifluoroacetyl-lysine NCA in 1,4-dioxane as solvent, and stirring until a clear solution is formed;
(2) adding diethylamine for catalysis, stirring at 20-25° C., then slowly pouring the reaction solution into water, collecting the produced white fully protected solid glatiramer, and drying it;
(3) adding the fully protected glatiramer obtained in step (2) to a solution of hydrobromic acid in acetic acid, stirring at 23.0-25.0° C., pouring the reaction solution into purified water for quenching when the reaction is over, stirring for 5 minutes, subjecting the mixture to suction filtration to obtain a yellow powdery solid trifluoroacetyl glatiramer, after repeating the steps of dissolving in water, suction filtration and drying 3-5 times, subjecting the solid trifluoroacetyl glatiramer to blast drying to remove the moisture therein; and
(4) dissolving the trifluoroacetyl glatiramer obtained in step (3) in a 1M piperidine aqueous solution at room temperature and stirring, subjecting the obtained solution to dialysis, adding glacial acetic acid to adjust the pH to 5.5-7.0, and obtaining white powdery glatiramer acetate after lyophilisation.

Preferably, the proportion of bromine in the form of elementary substance in the solution of hydrobromic acid in acetic acid ranges from 0.1% to 1%.

Preferably, in step (3), the solution of hydrobromic acid in acetic acid further contains 0.5~2% (wt %) of phenol, and most preferably, the solution contains 1% (wt %) of phenol.

In step (1), the volume of 1,4-dioxane is 200 ml, the mass ratio of L-alanine NCA, L-tyrosine NCA, L-glutamic acid-γ-benzyl ester NCA, and L-ε-trifluoroacetyl-lysine NCA is 2.59:1.036:1.974:4.693, and the stirring time is preferably 30 minutes.

In step (2), the ratio of diethylamine to 1,4-dioxane is 1:6 (v/v), and the ratio of the volume of the water into which the reaction mixture is poured to 1,4-dioxane is 2:1 (v/v), and the drying method of the fully protected glatiramer is preferably vacuum drying after suction filtration.

In step (3), the ratio of the solution of hydrobromic acid in acetic acid to the fully protected glatiramer is 10:0.74 (w/w), the reaction time is 19 hours, and the ratio of the purified water for quenching to the fully protected glatiramer is 100:3.7 (w/w).

In step (4), the ratio of trifluoroacetyl glatiramer to the volume of the 1M piperidine aqueous solution is 1:54 (w/v), the stirring time is preferably 24 hours, and the filter membrane used for dialysis is of 2 KDa.

In the glatiramer acetate prepared by the method according to the present invention, the content of bromo-tyrosine is 0.1% to 10%; if a solution of hydrobromic acid in acetic acid containing phenol is used in step (3), the content of bromo-tyrosine in the obtained glatiramer acetate is 0.1% to 0.5%.

DETAILED DESCRIPTION OF INVENTION

EXAMPLE 1

Figure 1:
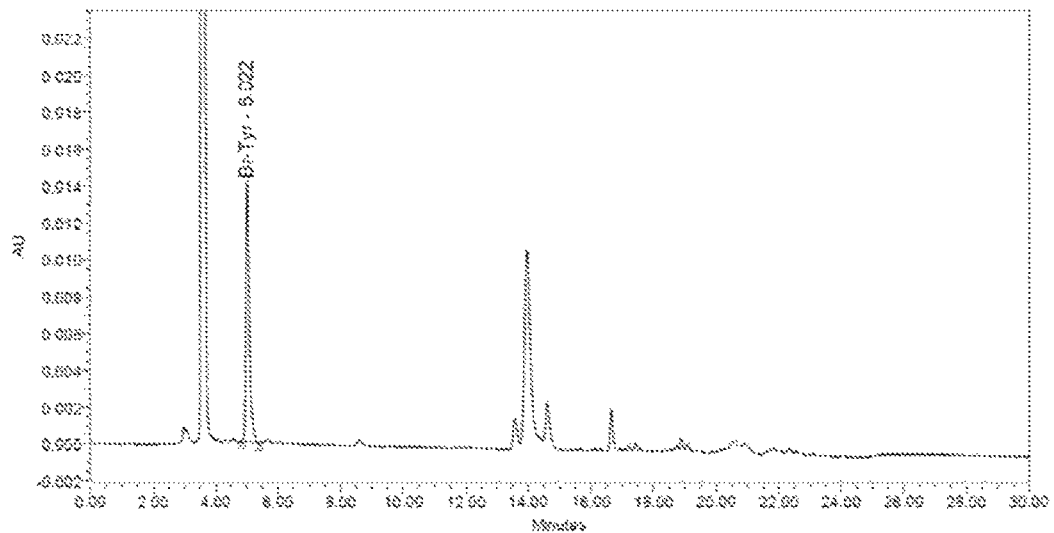
FIG. 1 is a chromatogram of a glatiramer acetate sample prepared in Example 2.
Figure 2:
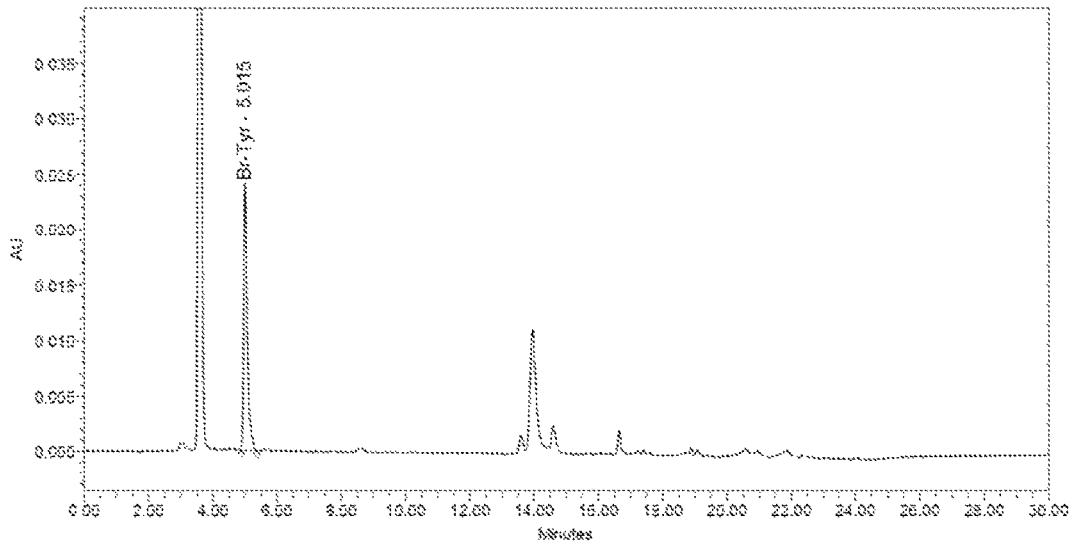
FIG. 2 is a chromatogram of a glatiramer acetate sample prepared in Example 3.
Figure 3:
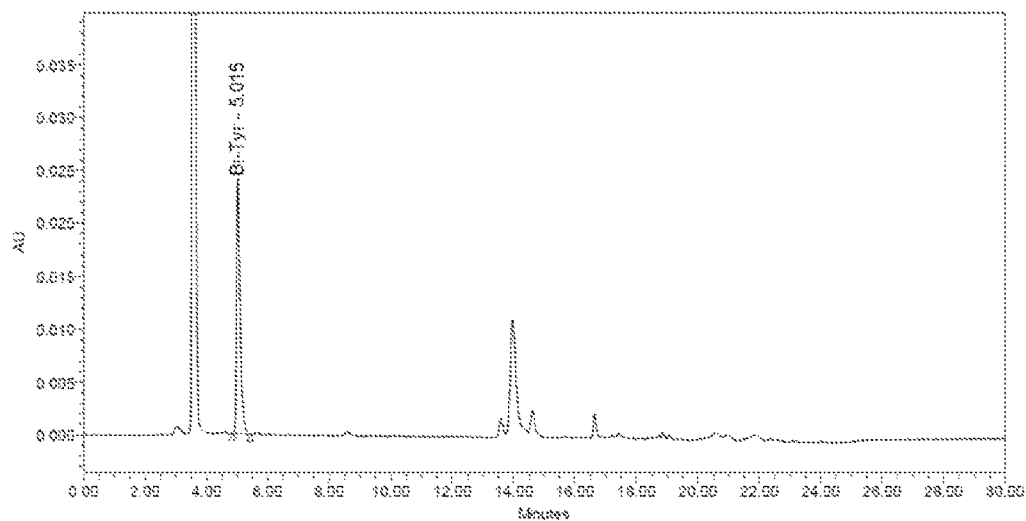
FIG. 3 is a chromatogram of a glatiramer acetate sample prepared in Example 4.
Figure 4:
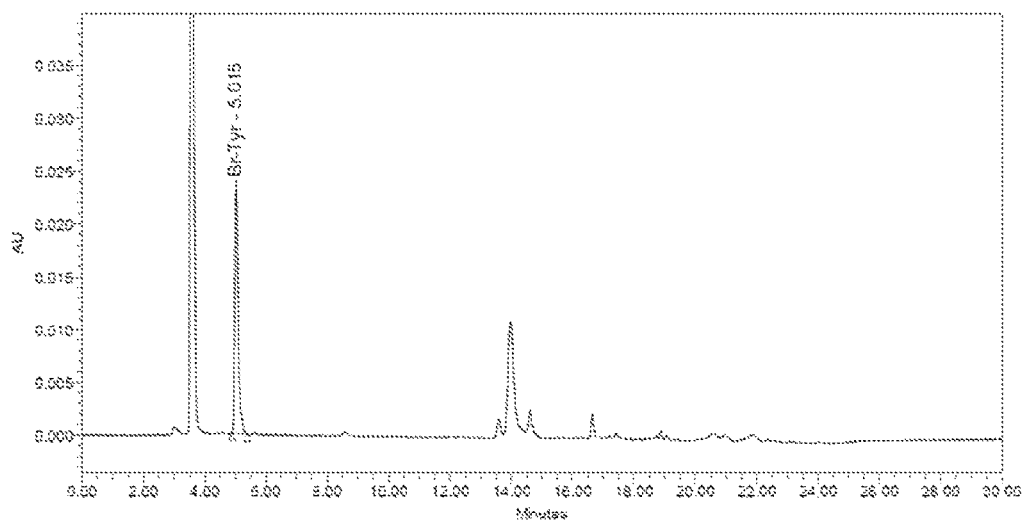
FIG. 4 is a chromatogram of a glatiramer acetate sample prepared in Example 5.
Figure 5:
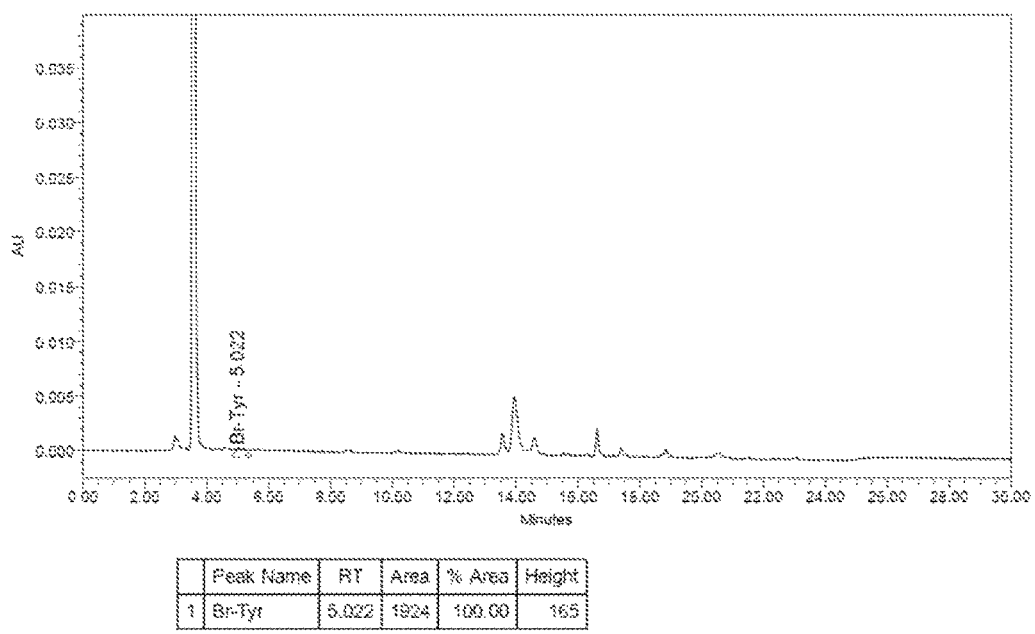
FIG. 5 is a chromatogram of a glatiramer acetate sample prepared in Example 6.

Preparation of Fully Protected Glatiramer 200 ml of 1,4-dioxane that had been treated with metal sodium was added in a three-necked bottle, 2.590 g of L-alanine NCA, 1.036 g of L-tyrosine NCA, 1.974 g of L-glutamic acid-γ-benzyl ester NCA, and 4.693 g of L-ε-trifluoroacetyl-lysine NCA were added at room temperature. The mixture was stirred for 30 minutes until it was clarified, and then 33 mg of diethylamine was added. The mixture was mechanically stirred for 24 hours at 20-25° C. The reaction mixture was poured into 400 ml of water, and a lot of white solid was generated. After suction filtration, 7.424 g of product was obtained by vacuum drying. The yield was 92.8%.

EXAMPLE 2

Preparation of Glatiramer Acetate (1)

10.0 g of a solution I of hydrobromic acid in acetic acid (in which the content of bromine in the form of elementary substance was 0.1%) was added into a reaction flask and stirred for 30 minutes. 0.74 g of fully protected glatiramer was added and stirred under a controlled temperature within 23.0-25.0° C. for 19 hours. The reaction mixture was poured into 20 ml of purified water for quenching, and stirred for 5 minutes. Yellow powdery solid was obtained after suction filtration. The solid was added into a container and 20 ml of water was added. The mixture was stirred for 10 minutes and then subjected to suction filtration. Above operations were repeated 4 times. The solid was subjected to blast drying for 12 hours (45° C.).

0.50 g of trifluoroacetyl glatiramer obtained in Example 2, and 27 ml of a 1M piperidine aqueous solution were added in a three-necked bottle, and stirred for 24 hours at room temperature. The mixture was subjected to dialysis with a 2 KDa filter membrane. The obtained solution was added with glacial acetic acid to adjust the pH to 5.5-7.0 and stirred for 1 hour. White powder was obtained after lyophilisation. The content of bromo-tyrosine was detected to be 6.51%.

EXAMPLE 3

Preparation of Glatiramer Acetate (2)

10.0 g of a solution II of hydrobromic acid in acetic acid (in which the content of bromine in the form of elementary substance was 0.3%) was added into a reaction flask and stirred for 30 minutes. 0.74 g of fully protected glatiramer was added and stirred under a controlled temperature within 23.0-25.0° C. for 19 hours. The reaction mixture was poured into 20 ml of purified water for quenching, and stirred for 5 minutes. Yellow powdery solid was obtained after suction filtration. The solid was added into a container and 20 ml of water was added. The mixture was stirred for 10 minutes and then subjected to suction filtration. Above operations were repeated 4 times. The solid was subjected to blast drying for 12 hours (45° C.).

0.50 g of trifluoroacetyl glatiramer obtained in Example 3, 27 ml of a 1M piperidine aqueous solution were added in a three-necked bottle, and stirred for 24 hours at room temperature. The mixture was subjected to dialysis with a 2 KDa filter membrane. The obtained solution was added with glacial acetic acid to adjust the pH to 5.5-7.0 and stirred for 1 hour. White powder was obtained after lyophilisation. The content of bromo-tyrosine was detected to be 9.30%.

EXAMPLE 4

Preparation of Glatiramer Acetate (3)

10.0 g of a solution III of hydrobromic acid in acetic acid (in which the content of bromine in the form of elementary substance was 0.5%) was added into a reaction flask and stirred for 30 minutes. 0.74 g of fully protected glatiramer was added and stirred under a controlled temperature within 23.0-25.0° C. for 19 hours. The reaction mixture was poured into 20 ml of purified water for quenching, and stirred for 5 minutes. Yellow powdery solid was obtained after suction filtration. The solid was added into a container and 20 ml of water was added. The mixture was stirred for 10 minutes and then subjected to suction filtration. Above operations were repeated 4 times. The solid was subjected to blast drying for 12 hours (45° C.).

0.50 g of trifluoroacetyl glatiramer obtained in Example 4, 27 ml of a 1M piperidine aqueous solution were added in a three-necked bottle and stirred for 24 hours at room temperature. The mixture was subjected to dialysis with a 2 KDa filter membrane. The obtained solution was added with glacial acetic acid to adjust the pH to 5.5-7.0 and stirred for 1 hour. White powder was obtained after lyophilisation. The content of bromo-tyrosine was detected to be 9.23%.

EXAMPLE 5

Preparation of Glatiramer Acetate (4)

10.0 g of a solution IV of hydrobromic acid in acetic acid (in which the content of bromine in the form of elementary substance was 0.7%) was added into a reaction flask and stirred for 30 minutes. 0.74 g of fully protected glatiramer was added and stirred under a controlled temperature within 23.0-25.0° C. for 19 hours. The reaction mixture was poured into 20 ml of purified water for quenching, and stirred for 5 minutes. Yellow powdery solid was obtained after suction filtration. The solid was added into a container and 20 ml of water was added. The mixture was stirred for 10 minutes and then subjected to suction filtration. Above operations were repeated 4 times. The solid was subjected to blast drying for 12 hours (45° C.).

0.50 g of trifluoroacetyl glatiramer obtained in Example 5, 27 ml of a 1M piperidine aqueous solution were added in a three-necked bottle, and stirred for 24 hours at room temperature. The mixture was subjected to dialysis with a 2 KDa filter membrane. The obtained solution was added with glacial acetic acid to adjust the pH to 5.5-7.0 and stirred for 1 hour. White powder was obtained after lyophilisation. The content of bromo-tyrosine was detected to be 9.11%.

EXAMPLE 6

Preparation of Glatiramer Acetate (5)

10.0 g of a solution IV of hydrobromic acid in acetic acid (in which the content of bromine in the form of elementary substance was 0.7%) and 0.1 g of phenol were added into a reaction flask and stirred for 30 minutes. 0.74 g of fully protected glatiramer was added and stirred under a controlled temperature within 23.0-25.0° C. for 19 hours. The reaction mixture was poured into 20 ml of purified water for quenching, and stirred for 5 minutes. Yellow powdery solid was obtained after suction filtration. The solid was added into a container and 20 ml of water was added. The mixture was stirred for 10 minutes and then subjected to suction filtration. Above operations were repeated 4 times. The solid was subjected to blast drying for 12 hours (45° C.).

0.50 g of trifluoroacetyl glatiramer obtained in Example 6, 27 ml of a 1M piperidine aqueous solution were added in a three-necked bottle, and stirred for 24 hours at room temperature. The mixture was subjected to dialysis with a 2 KDa filter membrane. The obtained solution was added with glacial acetic acid to adjust the pH to 5.5-7.0 and stirred for 1 hour. White powder was obtained after lyophilisation. The content of bromo-tyrosine was detected to be 0.11%.

A final note, the above examples are merely to help the skilled in the art understand the technical aspects of the present invention and should not be construed as limiting the actual scope of the present invention.

What is claimed is:

1. A method for preparing highly purified glatiramer acetate, comprising the following steps:
   (1) dissolving L-alanine NCA, L-tyrosine NCA, L-glutamic acid-γ-benzyl ester NCA, and L-ε-trifluoroacetyl-lysine NCA in 1,4-dioxane as solvent to form a first solution, then stirring the first solution until the first solution is clarified;
   (2) adding diethylamine to the first solution for catalysis, then stirring the first solution at 20-25° C. to form a second solution, then slowly pouring the second solution into water to form a third solution, then collecting white fully protected solid glatiramer produced in the third solution, and then drying the white fully protected solid glatiramer to obtain fully protected glatiramer;
   (3) adding a fourth solution of hydrobromic acid in acetic acid into a reactor, then adding the fully protected glatiramer to the reactor to form a fifth solution, then stirring the fifth solution at 23.0-25.0° C. to form a sixth solution, then pouring the sixth solution into purified water for quenching to form a seventh solution, then stirring the seventh solution for 5 minutes, then subjecting the seventh solution to suction filtration to obtain yellow powdery solid trifluoroacetyl glatiramer;
   (4) dissolving the yellow powdery solid trifluoroacetyl glatiramer in water to form an eighth solution, then subjecting the eighth solution to suction filtration to obtain the yellow powdery solid trifluoroacetyl glatiramer, and then drying the yellow powdery solid trifluoroacetyl glatiramer;
   (5) repeating step (4) 3-5 times;
   (6) subjecting the yellow powdery solid trifluoroacetyl glatiramer of step (5) to blast drying to remove the moisture in the yellow powdery solid trifluoroacetyl glatiramer; and
   (7) dissolving the yellow powdery solid trifluoroacetyl glatiramer of step (3) in a ninth 1M piperidine aqueous solution at room temperature to form a tenth solution and then stirring the tenth solution, then subjecting the tenth solution to dialysis to form a eleventh solution, then adding glacial acetic acid to the eleventh solution to adjust the pH of the eleventh solution to 5.5-7.0, and then subjecting the eleventh solution to lyophilisation to obtain white powdery glatiramer acetate.

2. The method according to claim 1, wherein a proportion of bromine in the form of elementary substance in the fourth solution ranges from 0.1% to 1%.

3. The method according to claim 1, wherein, in step (1), the volume of 1,4-dioxane is 200 ml, the mass ratio of L-alanine NCA, L-tyrosine NCA, L-glutamic acid-γ-benzyl ester NCA, and L-ε-trifluoroacetyl-lysine NCA is 2.59:1.036:1.974:4.693.

4. The method according to claim 1, wherein, in step (2), the ratio of diethylamine to 1,4-dioxane is 1:6 (v/v), and the ratio of the volume of the water into which the second solution is poured to 1,4-dioxane is 2:1 (v/v).

5. The method according to claim 1, wherein, in step (3), the ratio of the fourth solution to the fully protected glatiramer is 10:0.74 (w/w), the time for stirring the first solution at 20-25° C. is 19 hours, and the ratio of the purified water for quenching to the fully protected glatiramer is 100:3.7 (w/w).

6. The method according to claim 1, wherein, in step (7), the ratio of the yellow powdery solid trifluoroacetyl glatiramer to the volume of the ninth 1M piperidine aqueous solution is 1:54 (w/v), the stirring time of the tenth solution is 24 hours, and the filter membrane used for dialysis is a filter membrane of 2 KDa.

7. The method according to claim 1, wherein the the content of bromo-tyrosine in the obtained glatiramer acetate is 0.1% to 10%.

8. The method according to claim 2, wherein the the content of bromo-tyrosine in the obtained glatiramer acetate is 0.1% to 0.5%.

9. A method for preparing highly purified glatiramer acetate, comprising the following steps:
   (1) dissolving L-alanine NCA, L-tyrosine NCA, L-glutamic acid-γ-benzyl ester NCA, and L-ε-trifluoroacetyl-lysine NCA in 200 ml of 1,4-dioxane as solvent to form a first solution, and then stirring the first solution for 30 minutes until the first solution is clarified, wherein weights of the L-alanine, the L-tyrosine, the L-glutamic acid-γ-benzyl ester, and the L-ε-trifluoroacetyl-lysine are 2.59 g, 1.036 g, 1.974 g, and 4.693 g, respectively;
   (2) adding 33 mg of diethylamine to the first solution for catalysis, then stirring the first solution at 20-25° C. for 24 hours to form a second solution, then slowly pouring the second solution into 400 ml of water to form a third solution, then collecting white fully protected solid glatiramer produced in the third solution, and then drying the white fully protected solid glatiramer to obtain fully protected glatiramer;

(3) adding 10 g of a fourth solution of hydrobromic acid in acetic acid, in which the content of bromine in the form of elementary substance is 0.7% and the amount of phenol is 0.1 g, into a reaction flask, then stirring the fourth solution for 30 minutes, then adding 0.74 g of the fully protected glatiramer obtained in step (2) to the reaction flask to form a fifth solution, then stirring the fifth solution at 23.0-25.0° C. for 19 hours to form a sixth solution, then pouring the sixth solution into 20 ml of purified water for quenching to form a seventh solution, then stirring the seventh solution for 5 minutes, then subjecting the seventh solution to suction filtration to obtain yellow powdery solid trifluoroacetyl glatiramer;

(4) dissolving the yellow powdery solid trifluoroacetyl glatiramer in water to form an eighth solution, then subjecting the eighth solution to suction filtration to obtain the yellow powdery solid trifluoroacetyl glatiramer, and then drying the yellow powder solid trifluoroacetyl glatiramer;

(5) repeating step (4) 4 times;

(6) subjecting the yellow powdery solid trifluoroacetyl glatiramer of step (5) to blast drying at 45° C. for 12 hours to remove the moisture in the yellow powdery solid trifluoroacetyl glatiramer; and (7) dissolving 0.5 g of the yellow powdery solid trifluoroacetyl glatiramer obtained in step (3) in 27 ml of a ninth 1M piperidine aqueous solution at room temperature to form a tenth solution and then stirring the tenth solution for 24 hours, then subjecting the tenth solution to dialysis to form a eleventh solution through a filter membrane of 2 KDa, then adding glacial acetic acid to the eleventh solution to adjust the pH of the eleventh solution to 5.5-7.0, then stirring the eleventh solution for 1 hour, and then subjecting the eleventh solution to lyophilisation to obtain white powdery glatiramer acetate.

10. The method according to claim 2, wherein the fourth solution contains 0.5~2% (wt %) of phenol.

11. The method according to claim 10, wherein the fourth solution contains 1% (wt %) of phenol.

12. The method according to claim 3, wherein the stirring time of the first solution is 30 minutes.

13. The method according to claim 2, wherein, in step (1), the volume of 1,4-dioxane is 200 ml, the mass ratio of L-alanine NCA, L-tyrosine NCA, L-glutamic acid-γ-benzyl ester NCA, and L-ε-trifluoroacetyl-lysine NCA is 2.59: 1.036:1.974:4.693.

14. The method according to claim 13, wherein the stirring time of the first solution is 30 minutes.

15. The method according to claim 4, wherein, in step (2), the drying is vacuum drying after suction filtration.

16. The method according to claim 2, wherein, in step (2), the ratio of diethylamine to 1,4-dioxane is 1:6 (v/v), and the ratio of the volume of the water into which the second solution is poured to 1,4-dioxane is 2:1 (v/v).

17. The method according to claim 16, wherein, in step (2), the drying is vacuum drying after suction filtration.

18. The method according to claim 2, wherein, in step (3), the ratio of the fourth solution to the fully protected glatiramer is 10:0.74 (w/w), the stirring time of the first solution at 20-25° C. is 19 hours, and the ratio of the purified water for quenching to the fully protected glatiramer is 100:3.7 (w/w).

19. The method according to claim 2, wherein, in step (7), the ratio of the trifluoroacetyl glatiramer to the volume of the ninth 1M piperidine aqueous solution is 1:54 (w/w), the stirring time of the tenth solution is 24 hours, and the filter membrane used for dialysis is a filter membrane of 2 KDa.

* * * * *